(12) United States Patent
Andrews

(10) Patent No.: US 7,172,626 B1
(45) Date of Patent: Feb. 6, 2007

(54) METHOD FOR RECONSTRUCTING A KNEE

(76) Inventor: Scott A. Andrews, 5 Butterfield Cir., Flossmoor, IL (US) 60422

(*) Notice: Subject to any disclaimer, the term of this patent is extended or adjusted under 35 U.S.C. 154(b) by 0 days.

(21) Appl. No.: 11/126,639

(22) Filed: May 11, 2005

Related U.S. Application Data

(62) Division of application No. 10/166,474, filed on Jun. 10, 2002, now Pat. No. 6,949,102.

(51) Int. Cl.
A61F 2/08 (2006.01)
(52) U.S. Cl. .................................................. 623/13.13
(58) Field of Classification Search ..... 623/13.11–13.2
See application file for complete search history.

(56) References Cited

U.S. PATENT DOCUMENTS 6,353,982 B1 * 3/2002 Looker et al. ................. 24/302
6,679,889 B1 * 1/2004 West et al. .................... 606/88
2003/0176920 A1 * 9/2003 Sklar et al. ............... 623/13.13

* cited by examiner

Primary Examiner—Bruce Snow
(74) Attorney, Agent, or Firm—Thomas R. Vigil

(57) ABSTRACT

The equal tension applying device is used to apply equal tension to a group of tendons. The device comprises a 3 to 9 inch elongate flexible member and a hook at each end of the flexible member. Typically a torn ACL is replaced with two loops of tendons defining 4 tendon strands. The ends of each strand have sutures therein. The tendon loops are fixed in a femoral tunnel with a fixation pin and extend into and through a tibial tunnel. The method includes the steps of: tying the ends of the sutures together to form a loop, placing a hook of the elongate tensioning device over the suture loop, applying tension on the device, followed by anchoring the ends of the tendon strands to the tibia.

3 Claims, 5 Drawing Sheets

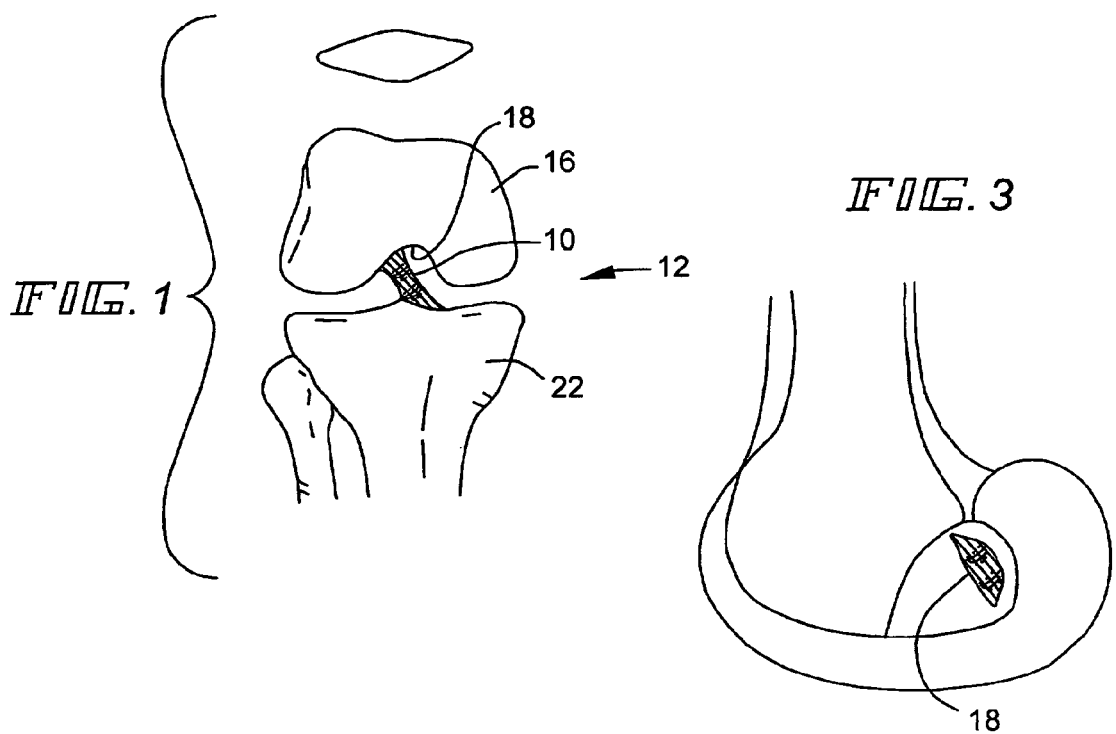
FIG. 1
FIG. 3
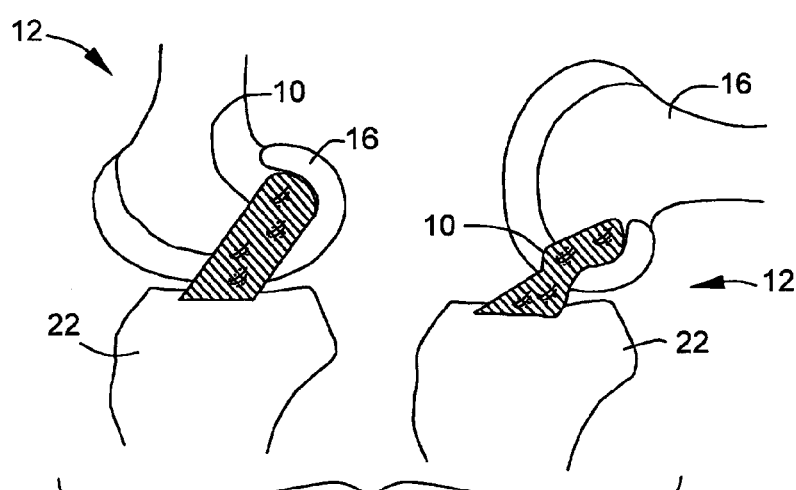
FIG. 2
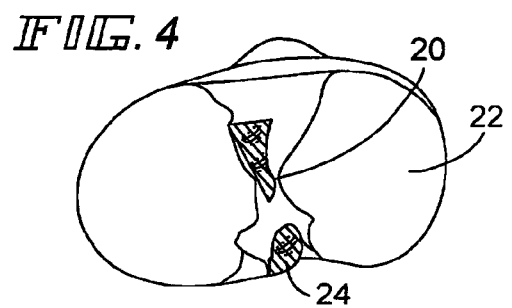
FIG. 4

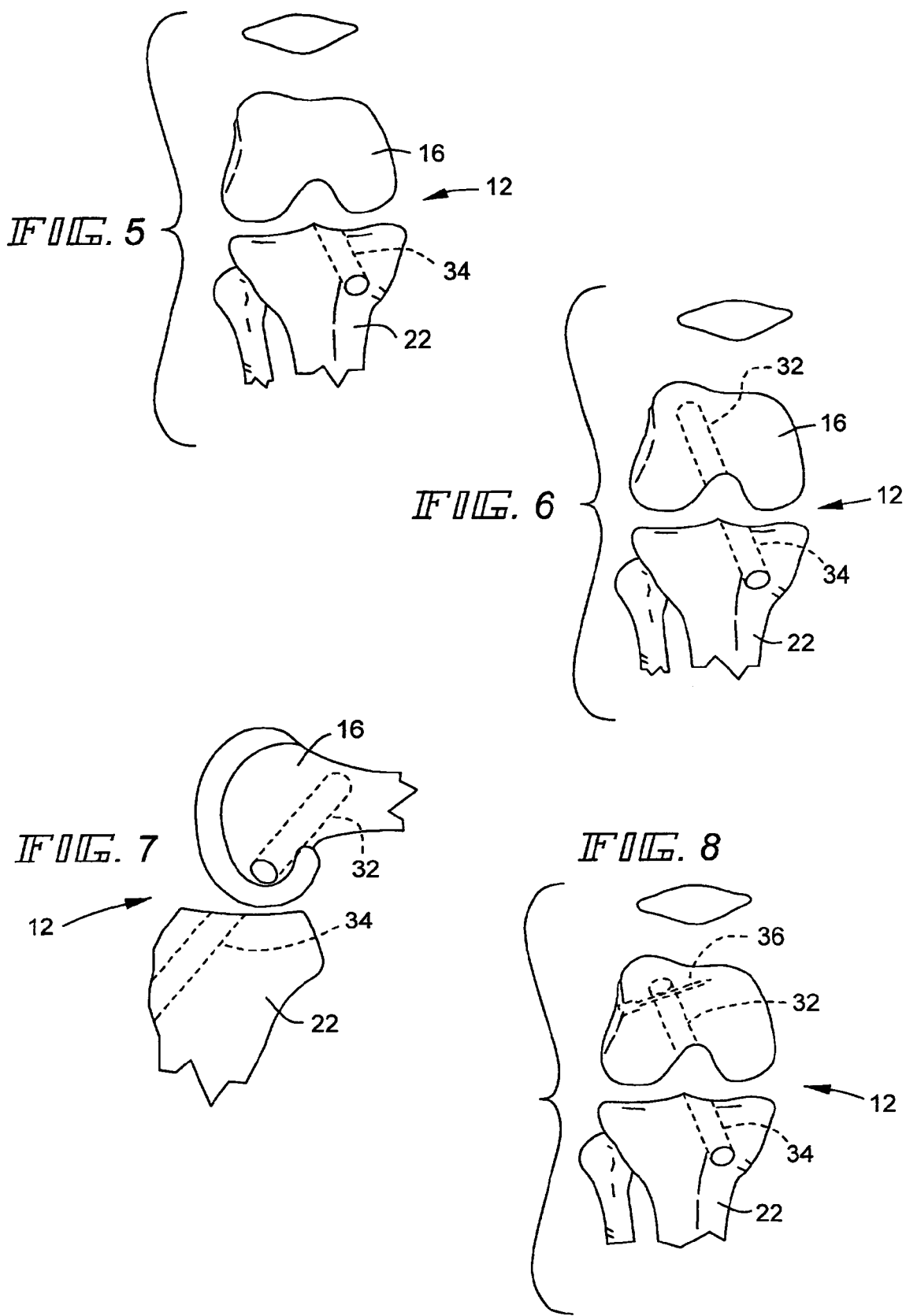

FIG. 9
FIG. 10
FIG. 11
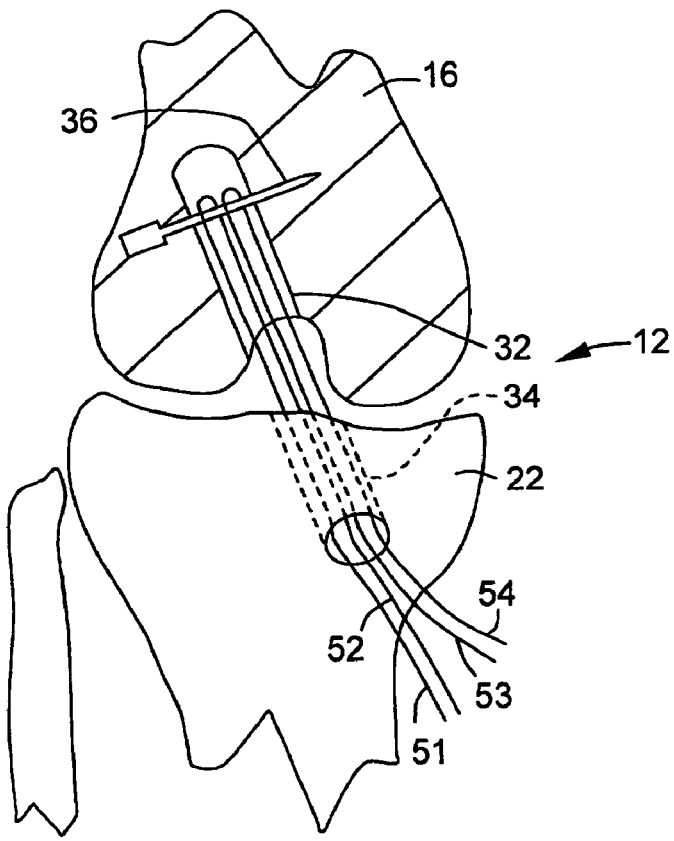
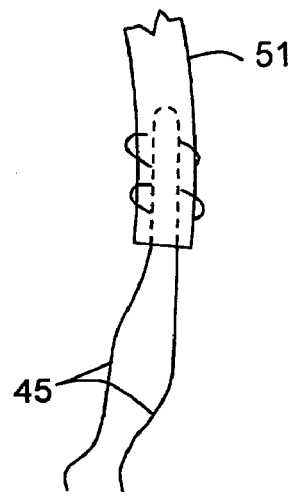

METHOD FOR RECONSTRUCTING A KNEE

This application is a divisional of Ser. No. 10/166,474, filed Jun. 10, 2002, now U.S. Pat. No. 6,949,102.

BACKGROUND OF THE INVENTION

1. Field of the Invention

The present invention relates to a method and device for applying equal tension on two or more tendons as they are being attached to a tibia in knee reconstruction surgery.

2. Description of Related Art

The Anterior Cruciate Ligament (ACL) is a short (2.5–5.0 cm) stout ligament in the center of the knee. This ligament generally attaches on the femur in the postero-lateral aspect of the inter-condylar notch. The other end of the ACL attaches to the tibia in the center of the tibial plateau just anterior to the Posterior cruciate ligament (PCL) attachment. The main function of the ACL is to resist anterior translation of the tibia in reference to the femur.

When this ligament is torn, the knee loses some of its stability and this can lead to symptoms such as giving way, effusions and pain. Also other structures in the knee are at risk for damage with a torn ACL such as the menisci and cartilage surfaces.

Because of these problems, if a person suffers an injury resulting in a tear of the ACL, it is frequently recommended to reconstruct this ligament, as it has no ability to heal itself.

ACL reconstruction attempts to replace the torn or insufficient ACL with tissue (graft) that will replicate its function as much as possible.

In ACL reconstruction there are three main issues, which need to be addressed:

1) Strong fixation of the graft on the femoral side and an intra-articular exit point (femoral side) that mirrors the attachment of the native ACL.
2) Strong center (intra-articular) portion of the graft, which mimics or surpasses the strength and other properties (e.g. stiffness, flexibility, tension) of the native ACL.
3) Strong fixation of the graft on the tibial side and an intra-articular exit point (tibial side) that mirrors the attachment of the native ACL.

A common graft used in ACL reconstruction is the harvested tendons of both the Semitendinosus and Gracilis hamstring muscles. These tendons are commonly doubled over in most surgeries making a graft complex, which has 4 strands. This 4-strand complex surpasses the strength and stiffness of most native ACLs. These properties are best realized when the tension in each of the 4 strands is equal.

In order to address issues 1 and 3 from above, tunnels are commonly drilled into both the femur and tibia. The tunnels allow for strong fixation (and biologic attachment) of the graft within them and the intra-articular exits of the tunnels reflect the attachment sites of the native ACL.

In general the tibial tunnel is drilled first and then the femoral tunnel is drilled. Fixation within the tunnels usually is accomplished first on the femoral side. The most common method entails a transfixing pin or post that crosses the tunnel at a 90° angle. The tendons go around this pin (which is fixed in the bone) and this doubles the tendons while also providing fixation on the femoral side.

Starting at the transfixing pin (in the femoral tunnel) the 4 strands of the tendons go through the remainder of the femoral tunnel, and then exit into the joint, traverse the joint, then go into the tibial tunnel and finally exit anteriorly out of the tibia.

Fixation on the tibial side is commonly achieved with the use of spiked washers and screws, staples, or other specialized screws.

Prior to the fixation on the tibial side, the tendons are placed under tension by pulling on the sutures that are attached to the ends of the tendons. While pulling on the tendons the fixation device is applied on the tibial side. This completes the procedure.

Examples of non-analogous devices used in knee reconstruction procedures are disclosed in the following non-analogous U.S. Patents.

| U.S. PAT. NO. | PATENTEE |
|---|---|
| 5,628,756 | Barker et al. |
| 5,646,266 | Li |
| 6,036,694 | Goble et al. |
| 6,056,752 | Roger |
| 6,214,007 | Anderson |
| 6,152,928 | Wenstrom, Jr. |
| 6,235,057 | Roger et al. |
| 6,290,711 | Caspari et al. |

BRIEF SUMMARY OF THE INVENTION

The present invention teaches a method for applying equal tension to several, typically four, tendons before and as they are attached to a tibia in a knee reconstruction procedure. The present invention also is directed to a device comprising a flexible line, suture, cable, rope, cord, chain, or wire having a hook formation at each end.

In practicing the method, sutures are fixed, respectfully, to the ends of each tendons, and tied together to form a loop. Then, the device is inserted through the loop and the hook formations are hooked on a bar or rod. Tension is placed on the rod or bar by pulling on same

BRIEF DESCRIPTION OF THE SEVERAL VIEWS OF THE DRAWINGS

FIG. 1 is a front to back (anterior-posterior or AP) view of a knee;

FIG. 2 is a cross-sectional (sagittal) view of the knee shown in FIG. 1;

FIG. 3 is a cross-sectional (sagittal) view of a distal femur and shows the Anterior Cruciate Ligament (ACL) attachment site;

FIG. 4 is an axial view of a tibia showing the ACL attachment site;

FIG. 5 is an front to back (AP) view of the knee and shows a tibial tunnel which is generally drilled first;

FIG. 6 is a front to back (AP) view of the knee and shows the tibial tunnel and a femoral tunnel which is generally drilled by going through the tibial tunnel;

FIG. 7 is a cross-sectional (sagittal) view of the knee and shows the tibial tunnel and the femoral tunnel;

FIG. 8 is a front to back (AP) view of the knee with a transfixing pin crossing the femoral tunnel;

FIG. 9 is a cross-sectional (AP) view of the knee shows two hamstring tendons going through both tunnels and the knee joint and around the transfixing pin which doubles them, making four strands of tendons going through the tunnels, and the transfixing pin provides a femoral fixation;

FIG. 10 is a plan view of the end of a tendon with suture thread going through the tendon and coming out the end of the tendon;

FIG. 11 is a perspective view of a tendon looped around a transfixing pin and shows suture threads at each end of the tendon tied together to form a large loop;

DETAILED DESCRIPTION OF THE INVENTION

Figure 12:
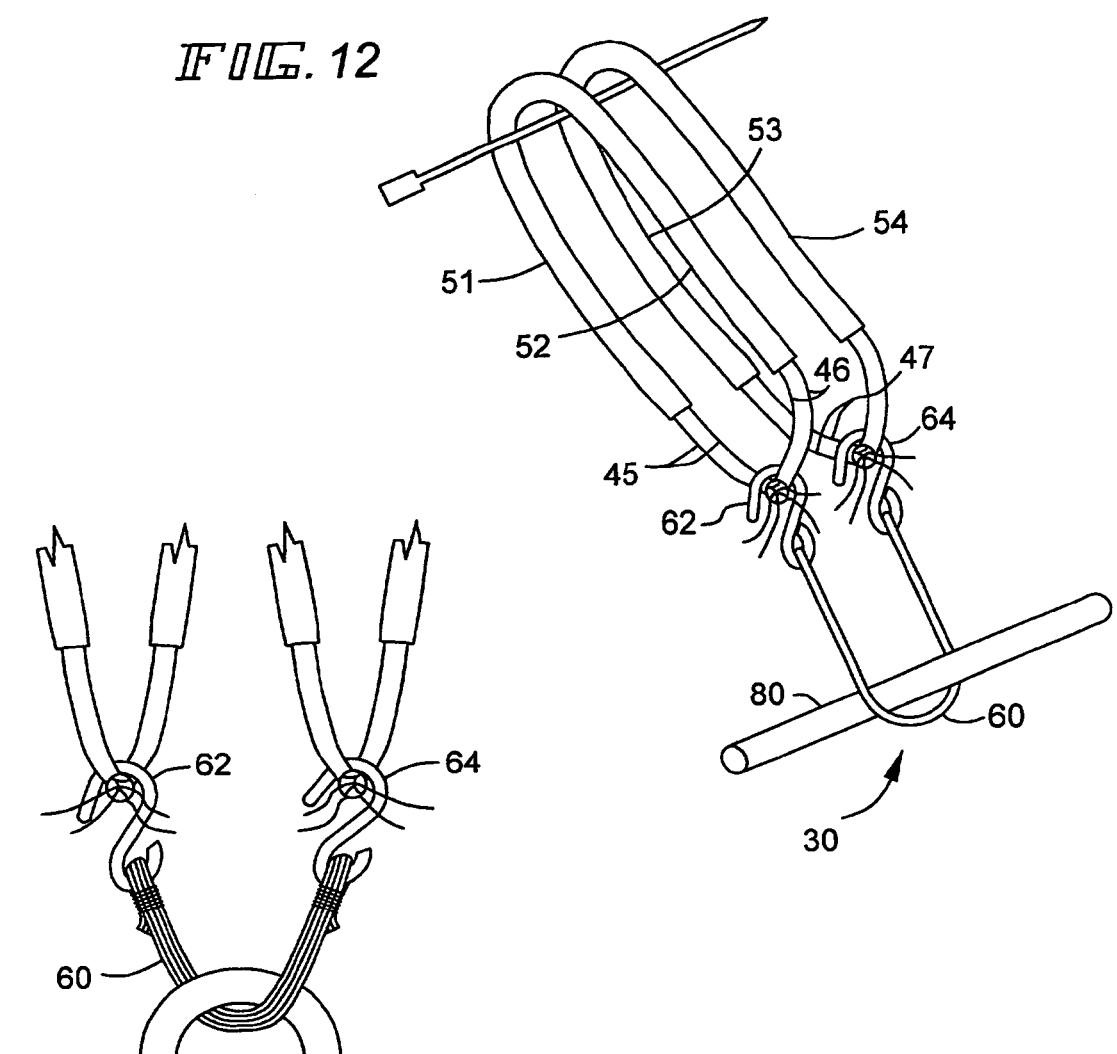
FIG. 12 is a perspective view of two tendons looped around a transfixing pin and shows suture threads at each end of each tendon tied together to form two large loops which are positioned in a tunnel to form the overall graft complex with the tendons looped around the transfixing pin and an elongate, flexible, tensioning device, which has a hook at each end and which is constructed according to the teachings of the present invention, hooked onto and between each pair of tied sutures with a pull bar extending through the now looped tensioning device for applying equal tension to the tendons of the tendon graft.

The Anterior Cruciate Ligament (ACL) 10 is a short (2.5–5.0 cm) stout ligament in the center of a knee 12 (FIGS. 1,2). This ligament 10 generally attaches on a femur 16 in the postero-lateral aspect of the inter-condylar notch 18 (FIG. 3). The other end 20 of the ACL attaches to a tibia 22 in the center of the tibial plateau just anterior to the Posterior Cruciate Ligament 24 (PCL) (FIG. 4).

The main function of the ACL 10 is to resist anterior translation of the tibia 22 in reference to the femur 16. When this ligament 10 is torn, the knee 12 loses some of its stability and this can lead to symptoms such as giving way, effusions and pain. Also other structures in the knee 12 are at risk for damage with a torn ACL 10 such as the menisci and cartilage surfaces. Because of these problems if a person suffers an injury resulting in a tear of the ACL 10, it is frequently recommended to reconstruct this ligament, as it has no ability to heal itself.

ACL reconstruction attempts to replace the torn or insufficient ACL 10 with tissue (graft) that will replicate its function as much as possible.

In ACL reconstruction the three main issues which need to be addressed are:

Strong fixation of the graft on the femoral side and an intra-articular exit point (femoral side) that mirrors the attachment of the native ACL.

Strong center (intra-articular) portion of the graft, which mimics or surpasses the strength and other properties (e.g. stiffness, flexibility, tension) of the native ACL.

Strong fixation of the graft on the tibial side and an intra-articular exit point (tibial side) that mirrors the attachment of the native ACL.

A common graft used in ACL reconstruction is the harvested tendons of both the Semitendinosus and Gracilis hamstring muscles. These tendons are commonly doubled over in most surgeries making a graft complex which has 4 strands. This 4-strand complex surpasses the strength and stiffness of most native ACLs. These properties are best realized when the tension in each of the 4 strands is equal.

It is therefore an object of the present invention to provide a flexible tensioning device 30 (FIG. 16) for use in a knee reconstruction procedure to be described below.

In order to address the first and third issues, tunnels 32 and 34 are commonly drilled into both the femur 16 and tibia 22. The tunnels 32 and 34 allow for strong fixation (and biologic attachment) of the graft within them and the intra-articular exits of the tunnels 32 and 34 reflect the attachment sites of the native ACL 10.

In general the tibial tunnel 34 is drilled first (FIG. 5) and then the femoral tunnel 32 is drilled (FIGS. 6 and 7). Fixation within the tunnels 32 and 34 usually is accomplished first on the femoral side. The most common method entails a transfixing pin or post 36 that crosses the tunnel 32 at a 90° angle (FIG. 8). A pair of tendons 40 and 42 (FIG. 9) go around this pin 36 (which is fixed in the bone) and this doubles the tendons 40, 42 while also providing fixation on the femoral side.

Starting at the transfixing pin 36 (in the femoral tunnel) the 4 strands of the tendons 40 and 42 (i.e. 51, 52, 53, 54) go through the remainder of the femoral tunnel 32, and then exit into the joint, traverse the joint, then go into the tibial tunnel 34 and finally exit anteriorly out of the tibia 22 (FIG. 9).

Figure 15:
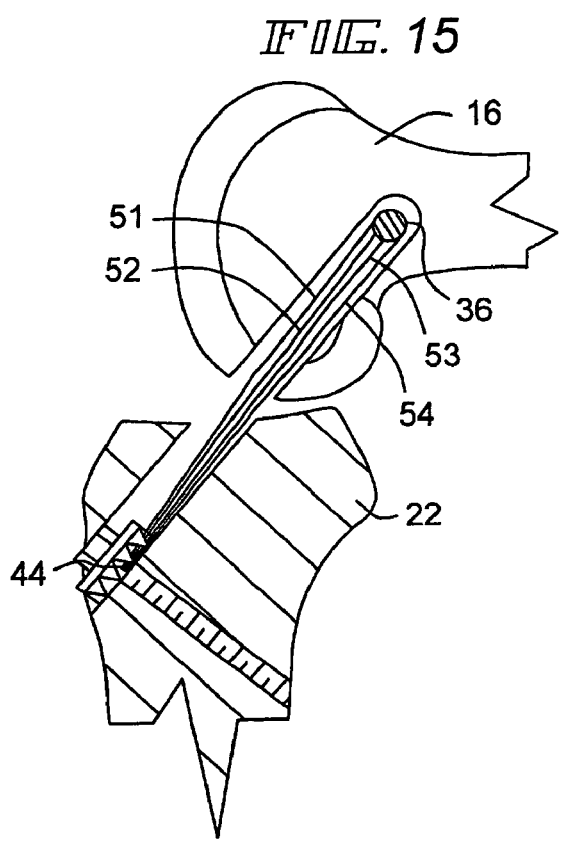

Fixation on the tibial side is commonly achieved with the use of spiked washers and screws, staples, or other specialized screws, such as the screw 44 shown in FIG. 15.

Prior to the fixation on the tibial side, the tendons 40 and 42 are placed under tension by pulling on sutures 45, 46, 47 and 48 which have been tied together and which are attached to ends of tendon strands 51–54 of the tendons 51, 52, 53, 54 (FIG. 12). While pulling on the looped sutures 45–48, a fixation device, screw 44, is applied on the tibial side to fix the tendons 40 and 42 (FIGS. 14,15) in place. This completes the procedure.

According to the teachings of the present invention, the tensioning device 30 is provided for enabling a medical technician, e.g., a nurse, to place equal tension on all four tendon strands 51–54 prior to anchoring the ends of the strands 51–54 in the tibia 20. As best seen in FIGS. 12–15, the device 30 comprises a 3–9 inch flexible, segment, line, suture, cable, rope, strip or chain 60 with a hook 62 or 64 at each end. One center segment 60 in a prototype was approximately 5 inches long, was made of a non-elastic material and had 1¼ inch hooks at each end for a total length of approximately 7½ inches.

Figure 14:
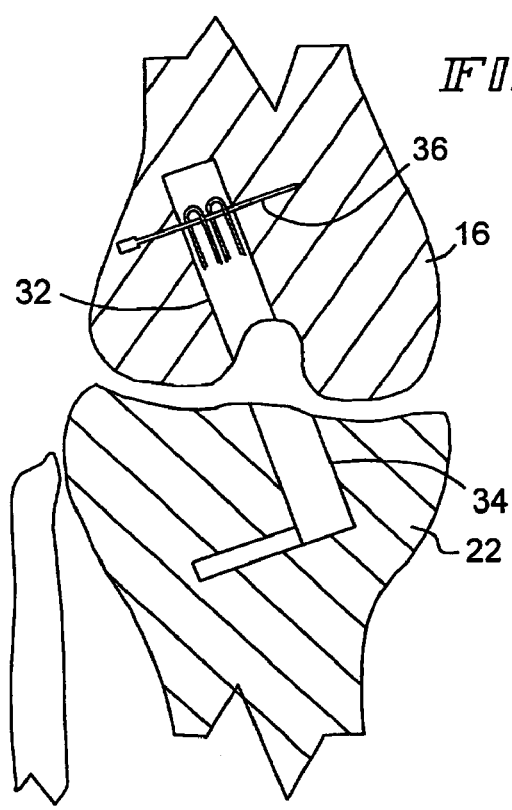
FIG. 14 is a fragmentary front to back (AP) view of the knee and shows part of the final ACL reconstruction and shows the femoral ends of the tendons fixed in plane with the tibial ends of the tendons omitted, and, FIG. 15 is a cross-sectional (sagittal) view of the knee with the final ACL reconstruction completed and shows fixation of the ends of the tendons in the femur and in the tibia.

The device 30 is used just prior to the fixation on the tibial side. Each of the four strands 51–54 of the tendons that exit the tibial tunnel has two suture threads 45, 46, 47 or 48 attached to the ends of the strands 51–54 (FIG. 10). The suture threads 45, 46 or 47, 48 of the same tendon 40 or 42 are tied together to form a large loop (FIG. 11). The hooks of the tensioning device 30 then capture each "suture portion" of the loop (FIG. 12). The surgeon then places a pull bar 80 through the flexible center section of the device 30 and pulls with appropriate force (surgeon preference). With the free movement of the hooks 62, 64 along the suture portion and the free movement of the tensioning device 30 on the pull bar 80, the tension in each of the strands 51–54 will be equal. While maintaining this tension, the surgeon then applies the tibial fixation device 44 (surgeon preference) (FIGS. 14,15).

Figure 16:
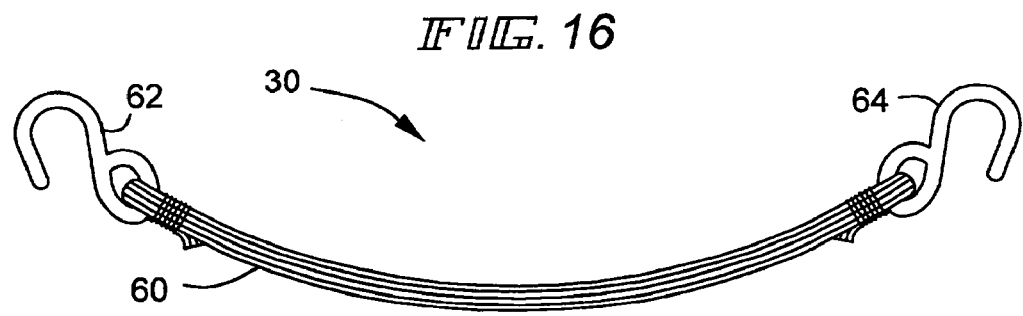
FIG. 16 is a plane view of the tensioning device of the present invention.

A plan view of the tensioning device 30 is shown in FIG. 16.

Figure 13:
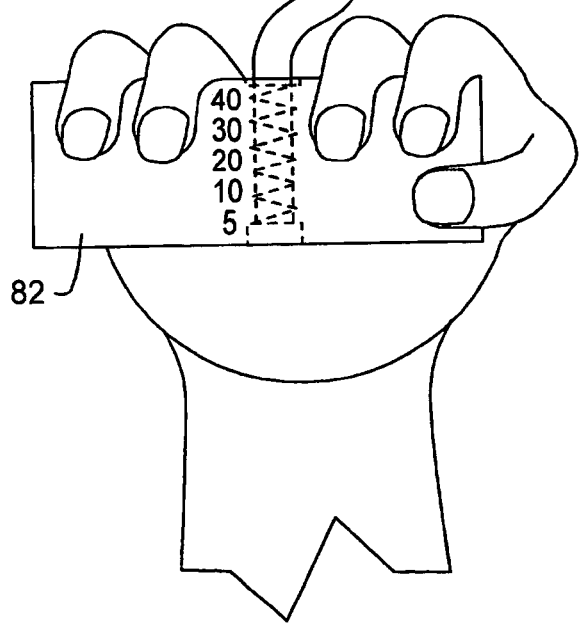
FIG. 13 is a plan view of a modified embodiment of an equal tension applying arrangement where a tensiometer is located in the line of pull on the graft complex to monitor the amount of tension applied.

In FIG. 13 there is illustrated a modified procedure where a tensiometer device 82 pulls the tensioning device 30 instead of the pull bar 80. This allows one to measure the tension on the graft complex while performing the tibial fixation. The tension is generally around 15 lbs. (range 5–40 lbs.).

Typically, while an assistant (intern or nurse) pulls on the tensioning device 30 with the pull bar 80 or through the tensiometer, thereby maintaining an appropriate desired tension on the graft complex of the tendons 51, 52, 53, 54, the surgeon applies the tibial fixation device, such as the screw 44.

From the foregoing description, it will be understood that the tensioning device 30 and the method for using same of the present invention have a number of advantages, some of which have been described above and others of which are inherent in the invention.

Also, modifications can be made to the tensioning device 30 and the method for using same without departing from the teachings of the invention.

Accordingly, the scope of the invention is only to be limited as necessitated by the accompanying claims.

I claim:

1. In a method for reconstructing a knee, wherein a torn ACL is replaced with two loops of tendons defining four tendon strands, the ends of each strand having sutures therein, the tendon loops being fixed in a femoral tunnel with a fixation pin and extending into and through a tibial tunnel, the improvement residing in the steps of:

tying the ends of each tendon together to form two tendon loops, providing an elongate tensioning device comprising a three to nine inch long, flexible, non-elastic suture, string or cord having a first end and a second end and first and second hooks, each hook being fixed to one end of the suture, string or cord, placing each hook of the elongate tensioning device over one of the two tendon loops, applying tension on the elongate tensioning device to apply tension on the four tendon strands, followed by anchoring the ends of the four tendon strands to the tibia.

2. The method of claim 1 including, the step of monitoring the tension applied to the four tendon strands.

3. In a method for reconstructing a knee, wherein a torn ACL is replaced with two loops of tendons defining four tendon strands, the ends of each strand having sutures therein, the tendon loops being fixed in a femoral tunnel with a fixation pin and extending into and through a tibial tunnel, the improvement residing in the steps of:

tying the ends of each tendon together to form two tendon loops, providing an elongate tensioning device comprising a flexible, non-elastic suture, string or cord with a hook fixed to each end of the suture, string or cord, placing each hook of the elongate tensioning device in one of the tendon loops thereby creating a flexible device loop with the suture, string or cord;

inserting a rigid rod through the flexible device loop;

followed by gripping the rod and pulling on same to place equal tension on the four tendon strands.

* * * * *